United States Patent [19]

Soulillou

[11] Patent Number: 5,672,486
[45] Date of Patent: Sep. 30, 1997

[54] PROTEIN POLYLIGANDS JOINED TO A STABLE PROTEIN CORE

[75] Inventor: Jean-Paul Soulillou, Nantes Cedex, France

[73] Assignee: Centre Hospitalier Regional de Nantes, Nantes Cedex, France

[21] Appl. No.: 932,915

[22] Filed: Aug. 20, 1992

Related U.S. Application Data

[63] Continuation of Ser. No. 646,875, Jan. 28, 1991, abandoned, which is a continuation-in-part of Ser. No. 575,394, Aug. 29, 1990, abandoned.

[51] Int. Cl.$^6$ .............................. C12N 15/00; C12N 5/00; C12P 21/06; C07H 21/04
[52] U.S. Cl. .................. 435/69.1; 435/240.2; 536/23.51; 536/23.53; 536/23.4; 536/23.1
[58] Field of Search .................... 435/69.1, 240.2; 935/1, 10, 15; 536/23.51, 23.53, 23.4

[56] References Cited

U.S. PATENT DOCUMENTS 4,935,352  6/1990  Koichi et al. ................. 435/69.52

FOREIGN PATENT DOCUMENTS

| 0 314 317 | 3/1988 | European Pat. Off. . |
|---|---|---|
| 0325262 | 7/1989 | European Pat. Off. . |
| 0 375 562 | 12/1989 | European Pat. Off. . |
| WO92/08495 | 5/1992 | WIPO . |

*Primary Examiner*—Suzanne E. Ziska
*Attorney, Agent, or Firm*—Flehr, Hohbach, Test, Albritton & Herbert

[57] ABSTRACT

Stable polyligands are provided by preparing fused proteins, where the fused protein comprises a ligand at one terminus and a subunit of a multimeric unit protein at the other terminus, where the fused protein is able to assemble to provide a polyligand. The polyligands find use in modulating physiological processes by inhibiting ligand induced signal transduction by surface membrane protein receptors and/or in the case of μ chain use, by complement mediated killing or any other effector functions. The molecule may be composed solely, of human components to avoid an immune response by the recipient.

8 Claims, 2 Drawing Sheets

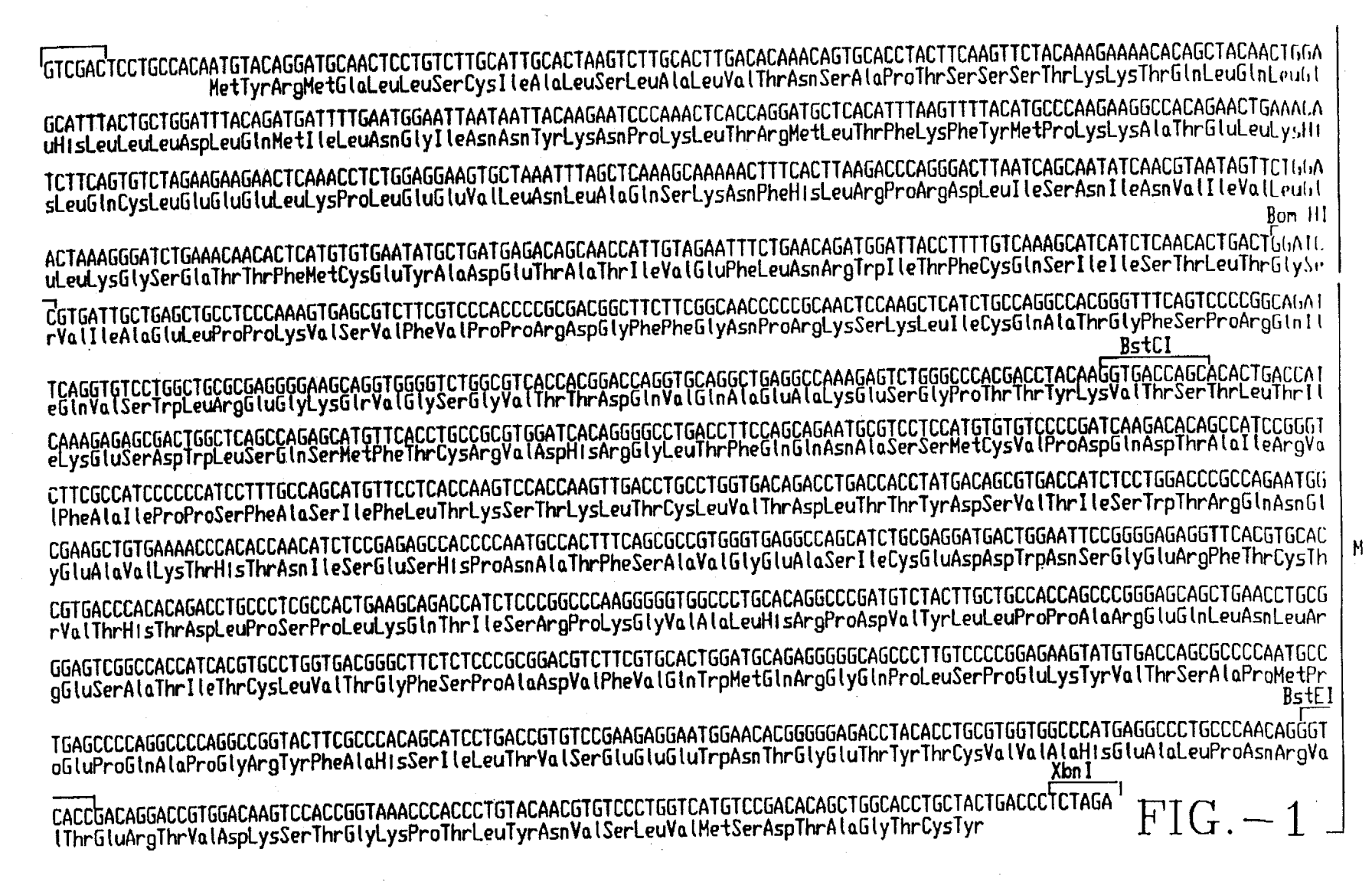

FIG. —1

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 1540 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 17..1528

( x i ) SEQUENCE DESCRIPTION: SEQ ID NO:1:

```
GTCGACTCCT GCCACA ATG TAC AGG ATG CAA CTC CTG TCT TGC ATT GCA        49
               Met Tyr Arg Met Gln Leu Leu Ser Cys Ile Ala
                1               5                   10

CTA AGT CTT GCA CTT GTC ACA AAC AGT GCA CCT ACT TCA AGT TCT ACA      97
Leu Ser Leu Ala Leu Val Thr Asn Ser Ala Pro Thr Ser Ser Ser Thr
            15                  20                  25

AAG AAA ACA CAG CTA CAA CTG GAG CAT TTA CTG CTG GAT TTA CAG ATG     145
Lys Lys Thr Gln Leu Gln Leu Glu His Leu Leu Leu Asp Leu Gln Met
        30                  35                  40

ATT TTG AAT GGA ATT AAT AAT TAC AAG AAT CCC AAA CTC ACC AGG ATG     193
Ile Leu Asn Gly Ile Asn Asn Tyr Lys Asn Pro Lys Leu Thr Arg Met
    45                  50                  55

CTC ACA TTT AAG TTT TAC ATG CCC AAG AAG GCC ACA GAA CTG AAA CAT     241
Leu Thr Phe Lys Phe Tyr Met Pro Lys Lys Ala Thr Glu Leu Lys His
60                  65                  70                  75

CTT CAG TGT CTA GAA GAA GAA CTC AAA CCT CTG GAG GAA GTG CTA AAT     289
Leu Gln Cys Leu Glu Glu Glu Leu Lys Pro Leu Glu Glu Val Leu Asn
                80                  85                  90

TTA GCT CAA AGC AAA AAC TTT CAC TTA AGA CCC AGG GAC TTA ATC AGC     337
Leu Ala Gln Ser Lys Asn Phe His Leu Arg Pro Arg Asp Leu Ile Ser
            95                  100                 105

AAT ATC AAC GTA ATA GTT CTG GAA CTA AAG GGA TCT GAA ACA ACA TTC     385
Asn Ile Asn Val Ile Val Leu Glu Leu Lys Gly Ser Glu Thr Thr Phe
        110                 115                 120

ATG TGT GAA TAT GCT GAT GAG ACA GCA ACC ATT GTA GAA TTT CTG AAC     433
Met Cys Glu Tyr Ala Asp Glu Thr Ala Thr Ile Val Glu Phe Leu Asn
    125                 130                 135

AGA TGG ATT ACC TTT TGT CAA AGC ATC ATC TCA ACA CTG ACT GGA TCC     481
Arg Trp Ile Thr Phe Cys Gln Ser Ile Ile Ser Thr Leu Thr Gly Ser
140                 145                 150                 155

GTG ATT GCT GAG CTG CCT CCC AAA GTG AGC GTC TTC GTC CCA CCC CGC     529
Val Ile Ala Glu Leu Pro Pro Lys Val Ser Val Phe Val Pro Pro Arg
                160                 165                 170

GAC GGC TTC TTC GGC AAC CCC CGC AAG TCC AAG CTC ATC TGC CAG GCC     577
```

|         |         |         |         |         |         |         |         |         |         |         |         |         |         |         |         |      |
|---------|---------|---------|---------|---------|---------|---------|---------|---------|---------|---------|---------|---------|---------|---------|---------|------|
| Asp | Gly | Phe | Phe | Gly | Asn | Pro | Arg | Lys | Ser | Lys | Leu | Ile | Cys | Gln | Ala | |
|     |     |     | 175 |     |     |     | 180 |     |     |     |     |     | 185 |     |     | |

| ACG | GGT | TTC | AGT | CCC | CGG | CAG | ATT | CAG | GTG | TCC | TGG | CTG | CGC | GAG | GGG | 625 |
|---|---|---|---|---|---|---|---|---|---|---|---|---|---|---|---|---|
| Thr | Gly | Phe | Ser | Pro | Arg | Gln | Ile | Gln | Val | Ser | Trp | Leu | Arg | Glu | Gly | |
| | | 190 | | | | | 195 | | | | | 200 | | | | |

| AAG | CAG | GTG | GGG | TCT | GGC | GTC | ACC | ACG | GAC | CAG | GTG | CAG | GCT | GAG | GCC | 673 |
|---|---|---|---|---|---|---|---|---|---|---|---|---|---|---|---|---|
| Lys | Gln | Val | Gly | Ser | Gly | Val | Thr | Thr | Asp | Gln | Val | Gln | Ala | Glu | Ala | |
| | 205 | | | | | 210 | | | | | 215 | | | | | |

| AAA | GAG | TCT | GGG | CCC | ACG | ACC | TAC | AAG | GTG | ACC | AGC | ACA | CTG | ACC | ATC | 721 |
|---|---|---|---|---|---|---|---|---|---|---|---|---|---|---|---|---|
| Lys | Glu | Ser | Gly | Pro | Thr | Thr | Tyr | Lys | Val | Thr | Ser | Thr | Leu | Thr | Ile | |
| 220 | | | | | 225 | | | | | 230 | | | | | 235 | |

| AAA | GAG | AGC | GAC | TGG | CTC | AGC | CAG | AGC | ATG | TTC | ACC | TGC | CGC | GTG | GAT | 769 |
|---|---|---|---|---|---|---|---|---|---|---|---|---|---|---|---|---|
| Lys | Glu | Ser | Asp | Trp | Leu | Ser | Gln | Ser | Met | Phe | Thr | Cys | Arg | Val | Asp | |
| | | | | 240 | | | | | 245 | | | | | 250 | | |

| CAC | AGG | GGC | CTG | ACC | TTC | CAG | CAG | AAT | GCG | TCC | TCC | ATG | TGT | GTC | CCC | 817 |
|---|---|---|---|---|---|---|---|---|---|---|---|---|---|---|---|---|
| His | Arg | Gly | Leu | Thr | Phe | Gln | Gln | Asn | Ala | Ser | Ser | Met | Cys | Val | Pro | |
| | | | | 255 | | | | | 260 | | | | | 265 | | |

| GAT | CAA | GAC | ACA | GCC | ATC | CGG | GTC | TTC | GCC | ATC | CCC | CCA | TCC | TTT | GCC | 865 |
|---|---|---|---|---|---|---|---|---|---|---|---|---|---|---|---|---|
| Asp | Gln | Asp | Thr | Ala | Ile | Arg | Val | Phe | Ala | Ile | Pro | Pro | Ser | Phe | Ala | |
| | | 270 | | | | | 275 | | | | | 280 | | | | |

| AGC | ATC | TTC | CTC | ACC | AAG | TCC | ACC | AAG | TTG | ACC | TGC | CTG | GTC | ACA | GAC | 913 |
|---|---|---|---|---|---|---|---|---|---|---|---|---|---|---|---|---|
| Ser | Ile | Phe | Leu | Thr | Lys | Ser | Thr | Lys | Leu | Thr | Cys | Leu | Val | Thr | Asp | |
| | 285 | | | | | 290 | | | | | 295 | | | | | |

| CTG | ACC | ACC | TAT | GAC | AGC | GTG | ACC | ATC | TCC | TGG | ACC | CGC | CAG | AAT | GGC | 961 |
|---|---|---|---|---|---|---|---|---|---|---|---|---|---|---|---|---|
| Leu | Thr | Thr | Tyr | Asp | Ser | Val | Thr | Ile | Ser | Trp | Thr | Arg | Gln | Asn | Gly | |
| 300 | | | | | 305 | | | | | 310 | | | | | 315 | |

| GAA | GCT | GTG | AAA | ACC | CAC | ACC | AAC | ATC | TCC | GAG | AGC | CAC | CCC | AAT | GCC | 1009 |
|---|---|---|---|---|---|---|---|---|---|---|---|---|---|---|---|---|
| Glu | Ala | Val | Lys | Thr | His | Thr | Asn | Ile | Ser | Glu | Ser | His | Pro | Asn | Ala | |
| | | | | 320 | | | | | 325 | | | | | 330 | | |

| ACT | TTC | AGC | GCC | GTG | GGT | GAG | GCC | AGC | ATC | TGC | GAG | GAT | GAC | TGG | AAT | 1057 |
|---|---|---|---|---|---|---|---|---|---|---|---|---|---|---|---|---|
| Thr | Phe | Ser | Ala | Val | Gly | Glu | Ala | Ser | Ile | Cys | Glu | Asp | Asp | Trp | Asn | |
| | | | 335 | | | | | 340 | | | | | 345 | | | |

| TCC | GGG | GAG | AGG | TTC | ACG | TGC | ACC | GTG | ACC | CAC | ACA | GAC | CTG | CCC | TCG | 1105 |
|---|---|---|---|---|---|---|---|---|---|---|---|---|---|---|---|---|
| Ser | Gly | Glu | Arg | Phe | Thr | Cys | Thr | Val | Thr | His | Thr | Asp | Leu | Pro | Ser | |
| | | 350 | | | | | 355 | | | | | 360 | | | | |

| CCA | CTG | AAG | CAG | ACC | ATC | TCC | CGG | CCC | AAG | GGG | GTG | GCC | CTG | CAC | AGG | 1153 |
|---|---|---|---|---|---|---|---|---|---|---|---|---|---|---|---|---|
| Pro | Leu | Lys | Gln | Thr | Ile | Ser | Arg | Pro | Lys | Gly | Val | Ala | Leu | His | Arg | |
| 365 | | | | | 370 | | | | | 375 | | | | | | |

| CCC | GAT | GTC | TAC | TTG | CTG | CCA | CCA | GCC | CGG | GAG | CAG | CTG | AAC | CTG | CGG | 1201 |
|---|---|---|---|---|---|---|---|---|---|---|---|---|---|---|---|---|
| Pro | Asp | Val | Tyr | Leu | Leu | Pro | Pro | Ala | Arg | Glu | Gln | Leu | Asn | Leu | Arg | |
| 380 | | | | | 385 | | | | | 390 | | | | | 395 | |

| GAG | TCG | GCC | ACC | ATC | ACG | TGC | CTG | GTG | ACG | GGC | TTC | TCT | CCC | GCG | GAC | 1249 |
|---|---|---|---|---|---|---|---|---|---|---|---|---|---|---|---|---|
| Glu | Ser | Ala | Thr | Ile | Thr | Cys | Leu | Val | Thr | Gly | Phe | Ser | Pro | Ala | Asp | |
| | | | | 400 | | | | | 405 | | | | | 410 | | |

| GTC | TTC | GTG | CAG | TGG | ATG | CAG | AGG | GGG | CAG | CCC | TTG | TCC | CCG | GAG | AAG | 1297 |
|---|---|---|---|---|---|---|---|---|---|---|---|---|---|---|---|---|
| Val | Phe | Val | Gln | Trp | Met | Gln | Arg | Gly | Gln | Pro | Leu | Ser | Pro | Glu | Lys | |
| | | | 415 | | | | | 420 | | | | | 425 | | | |

| TAT | GTG | ACC | AGC | GCC | CCA | ATG | CCT | GAG | CCC | CAG | GCC | CCA | GGC | CGG | TAC | 1345 |
|---|---|---|---|---|---|---|---|---|---|---|---|---|---|---|---|---|
| Tyr | Val | Thr | Ser | Ala | Pro | Met | Pro | Glu | Pro | Gln | Ala | Pro | Gly | Arg | Tyr | |
| | | 430 | | | | | 435 | | | | | 440 | | | | |

| TTC | GCC | CAC | AGC | ATC | CTG | ACC | GTG | TCC | GAA | GAG | GAA | TGG | AAC | ACG | GGG | 1393 |
|---|---|---|---|---|---|---|---|---|---|---|---|---|---|---|---|---|
| Phe | Ala | His | Ser | Ile | Leu | Thr | Val | Ser | Glu | Glu | Glu | Trp | Asn | Thr | Gly | |
| | 445 | | | | | 450 | | | | | 455 | | | | | |

| GAG | ACC | TAC | ACC | TGC | GTG | GTG | GCC | CAT | GAG | GCC | CTG | CCC | AAC | AGG | GTC | 1441 |
|---|---|---|---|---|---|---|---|---|---|---|---|---|---|---|---|---|
| Glu | Thr | Tyr | Thr | Cys | Val | Val | Ala | His | Glu | Ala | Leu | Pro | Asn | Arg | Val | |
| 460 | | | | | 465 | | | | | 470 | | | | | 475 | |

| ACC | GAG | AGG | ACC | GTG | GAC | AAG | TCC | ACC | GGT | AAA | CCC | ACC | CTG | TAC | AAC | 1489 |
|---|---|---|---|---|---|---|---|---|---|---|---|---|---|---|---|---|
| Thr | Glu | Arg | Thr | Val | Asp | Lys | Ser | Thr | Gly | Lys | Pro | Thr | Leu | Tyr | Asn | |
| | | | | 480 | | | | | 485 | | | | | 490 | | |

| GTG | TCC | CTG | GTC | ATG | TCC | GAC | ACA | GCT | GGC | ACC | TGC | TAC | TGACCCTCTA | | | 1538 |
|---|---|---|---|---|---|---|---|---|---|---|---|---|---|---|---|---|
| Val | Ser | Leu | Val | Met | Ser | Asp | Thr | Ala | Gly | Thr | Cys | Tyr | | | | |

| | | | | | | | | | | | | | | |
|---|---|---|---|---|---|---|---|---|---|---|---|---|---|---|
|Val|Ser|Leu|Val|Met|Ser|Asp|Thr|Ala|Gly|Thr|Cys|Tyr| | |
| | | |495| | | |500| | | | | | | |

GA                                                                                                                         1540

(2) INFORMATION FOR SEQ ID NO:2:

(i) SEQUENCE CHARACTERISTICS:
        (A) LENGTH: 504 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
|Met|Tyr|Arg|Met|Gln|Leu|Leu|Ser|Cys|Ile|Ala|Leu|Ser|Leu|Ala|Leu|
|1| | | |5| | | |10| | | | |15| | |
|Val|Thr|Asn|Ser|Ala|Pro|Thr|Ser|Ser|Ser|Thr|Lys|Lys|Thr|Gln|Leu|
| | | |20| | | | |25| | | | |30| | |
|Gln|Leu|Glu|His|Leu|Leu|Leu|Asp|Leu|Gln|Met|Ile|Leu|Asn|Gly|Ile|
| | |35| | | | |40| | | | |45| | | |
|Asn|Asn|Tyr|Lys|Asn|Pro|Lys|Leu|Thr|Arg|Met|Leu|Thr|Phe|Lys|Phe|
| |50| | | | |55| | | | |60| | | | |
|Tyr|Met|Pro|Lys|Lys|Ala|Thr|Glu|Leu|Lys|His|Leu|Gln|Cys|Leu|Glu|
|65| | | | |70| | | | |75| | | | |80|
|Glu|Glu|Leu|Lys|Pro|Leu|Glu|Glu|Val|Leu|Asn|Leu|Ala|Gln|Ser|Lys|
| | | | |85| | | | |90| | | | |95| |
|Asn|Phe|His|Leu|Arg|Pro|Arg|Asp|Leu|Ile|Ser|Asn|Ile|Asn|Val|Ile|
| | | |100| | | | |105| | | | |110| | |
|Val|Leu|Glu|Leu|Lys|Gly|Ser|Glu|Thr|Thr|Phe|Met|Cys|Glu|Tyr|Ala|
| | |115| | | | |120| | | | |125| | | |
|Asp|Glu|Thr|Ala|Thr|Ile|Val|Glu|Phe|Leu|Asn|Arg|Trp|Ile|Thr|Phe|
| |130| | | | |135| | | | |140| | | | |
|Cys|Gln|Ser|Ile|Ile|Ser|Thr|Leu|Thr|Gly|Ser|Val|Ile|Ala|Glu|Leu|
|145| | | | |150| | | | |155| | | | |160|
|Pro|Pro|Lys|Val|Ser|Val|Phe|Val|Pro|Pro|Arg|Asp|Gly|Phe|Phe|Gly|
| | | | |165| | | | |170| | | | |175| |
|Asn|Pro|Arg|Lys|Ser|Lys|Leu|Ile|Cys|Gln|Ala|Thr|Gly|Phe|Ser|Pro|
| | | |180| | | | |185| | | | |190| | |
|Arg|Gln|Ile|Gln|Val|Ser|Trp|Leu|Arg|Glu|Gly|Lys|Gln|Val|Gly|Ser|
| | |195| | | | |200| | | | |205| | | |
|Gly|Val|Thr|Thr|Asp|Gln|Val|Gln|Ala|Glu|Ala|Lys|Glu|Ser|Gly|Pro|
| |210| | | | |215| | | | |220| | | | |
|Thr|Thr|Tyr|Lys|Val|Thr|Ser|Thr|Leu|Thr|Ile|Lys|Glu|Ser|Asp|Trp|
|225| | | | |230| | | | |235| | | | |240|
|Leu|Ser|Gln|Ser|Met|Phe|Thr|Cys|Arg|Val|Asp|His|Arg|Gly|Leu|Thr|
| | | | |245| | | | |250| | | | |255| |
|Phe|Gln|Gln|Asn|Ala|Ser|Ser|Met|Cys|Val|Pro|Asp|Gln|Asp|Thr|Ala|
| | | |260| | | | |265| | | | |270| | |
|Ile|Arg|Val|Phe|Ala|Ile|Pro|Pro|Ser|Phe|Ala|Ser|Ile|Phe|Leu|Thr|
| | |275| | | | |280| | | | |285| | | |
|Lys|Ser|Thr|Lys|Leu|Thr|Cys|Leu|Val|Thr|Asp|Leu|Thr|Thr|Tyr|Asp|
| |290| | | | |295| | | | |300| | | | |
|Ser|Val|Thr|Ile|Ser|Trp|Thr|Arg|Gln|Asn|Gly|Glu|Ala|Val|Lys|Thr|
|305| | | | |310| | | | |315| | | | |320|
|His|Thr|Asn|Ile|Ser|Glu|Ser|His|Pro|Asn|Ala|Thr|Phe|Ser|Ala|Val|
| | | | |325| | | | |330| | | | |335| |

| Gly | Glu | Ala | Ser<br>340 | Ile | Cys | Glu | Asp | Asp<br>345 | Trp | Asn | Ser | Gly<br>350 | Glu | Arg | Phe |
|---|---|---|---|---|---|---|---|---|---|---|---|---|---|---|---|
| Thr | Cys | Thr<br>355 | Val | Thr | His | Thr | Asp<br>360 | Leu | Pro | Ser | Pro<br>365 | Leu | Lys | Gln | Thr |
| Ile | Ser | Arg<br>370 | Pro | Lys | Gly | Val<br>375 | Ala | Leu | His | Arg | Pro<br>380 | Asp | Val | Tyr | Leu |
| Leu<br>385 | Pro | Pro | Ala | Arg | Glu<br>390 | Gln | Leu | Asn | Leu | Arg<br>395 | Glu | Ser | Ala | Thr | Ile<br>400 |
| Thr | Cys | Leu | Val | Thr<br>405 | Gly | Phe | Ser | Pro | Ala<br>410 | Asp | Val | Phe | Val<br>415 | Gln | Trp |
| Met | Gln | Arg | Gly<br>420 | Gln | Pro | Leu | Ser | Pro<br>425 | Glu | Lys | Tyr | Val | Thr<br>430 | Ser | Ala |
| Pro | Met | Pro<br>435 | Glu | Pro | Gln | Ala | Pro<br>440 | Gly | Arg | Tyr | Phe | Ala<br>445 | His | Ser | Ile |
| Leu | Thr<br>450 | Val | Ser | Glu | Glu | Glu<br>455 | Trp | Asn | Thr | Gly | Glu<br>460 | Thr | Tyr | Thr | Cys |
| Val<br>465 | Val | Ala | His | Glu | Ala<br>470 | Leu | Pro | Asn | Arg | Val<br>475 | Thr | Glu | Arg | Thr | Val<br>480 |
| Asp | Lys | Ser | Thr | Gly<br>485 | Lys | Pro | Thr | Leu | Tyr<br>490 | Asn | Val | Ser | Leu<br>495 | Val | Met |
| Ser | Asp | Thr | Ala | Gly<br>500 | Thr | Cys | Tyr | | | | | | | | |

(2) INFORMATION FOR SEQ ID NO:3:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: synthetic DNA (xi) SEQUENCE DESCRIPTION: SEQ ID NO:3:

CGGATCCGTG ATTGCTGAGC TGCCTCCC 28

(2) INFORMATION FOR SEQ ID NO:4:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: synthetic DNA (xi) SEQUENCE DESCRIPTION: SEQ ID NO:4:

CTCTAGAGGG TCAGTAGCAG GTGCCAG 27

(2) INFORMATION FOR SEQ ID NO:5:

(i) SEQUENCE CHARACTERISTICS:
(A) LENGTH: 7 amino acids
(B) TYPE: amino acid
(D) TOPOLOGY: linear (ii) MOLECULE TYPE: peptide (xi) SEQUENCE DESCRIPTION: SEQ ID NO:5:

| Val | Ile | Ala | Glu | Leu | Pro | Pro |
|---|---|---|---|---|---|---|
| 1 | | | | 5 | | |

(2) INFORMATION FOR SEQ ID NO:6:

(i) SEQUENCE CHARACTERISTICS:
  (A) LENGTH: 28 base pairs
  (B) TYPE: nucleic acid
  (C) STRANDEDNESS: single
  (D) TOPOLOGY: linear (ii) MOLECULE TYPE: synthetic DNA (ix) FEATURE:
  (A) NAME/KEY: CDS
  (B) LOCATION: 1..15

(xi) SEQUENCE DESCRIPTION: SEQ ID NO:6:

```
GCT  GGC  ACC  TGC  TAC  TGACCCTCTA GAG                           28
Ala  Gly  Thr  Cys  Tyr
 1                    5
```

(2) INFORMATION FOR SEQ ID NO:7:

(i) SEQUENCE CHARACTERISTICS:
    (A) LENGTH: 5 amino acids
    (B) TYPE: amino acid
    (D) TOPOLOGY: linear (ii) MOLECULE TYPE: peptide (xi) SEQUENCE DESCRIPTION: SEQ ID NO:7:

```
Ala  Gly  Thr  Cys  Tyr
 1                    5
```

(2) INFORMATION FOR SEQ ID NO:8:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: synthetic DNA (xi) SEQUENCE DESCRIPTION: SEQ ID NO:8:

```
CGTCGACTCC TGCCACAATG TACAGG                                      26
```

(2) INFORMATION FOR SEQ ID NO:9:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: synthetic DNA (xi) SEQUENCE DESCRIPTION: SEQ ID NO:9:

```
CGGATCCAGT CAGTGTTGAG ATGATGC                                     27
```

(2) INFORMATION FOR SEQ ID NO:10:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: synthetic DNA (ix) FEATURE:
    (A) NAME/KEY: CDS
    (B) LOCATION: 1..21

(xi) SEQUENCE DESCRIPTION: SEQ ID NO:10:

```
AGC ATC ATC TCA ACA CTG ACT GGATCCG                                    2 8
Ser Ile Ile Ser Thr Leu Thr
 1               5
```

( 2 ) INFORMATION FOR SEQ ID NO:11:

( i ) SEQUENCE CHARACTERISTICS:
           ( A ) LENGTH: 7 amino acids
           ( B ) TYPE: amino acid
           ( D ) TOPOLOGY: linear ( i i ) MOLECULE TYPE: peptide ( x i ) SEQUENCE DESCRIPTION: SEQ ID NO:11:

```
Ser Ile Ile Ser Thr Leu Thr
 1               5
```

PROTEIN POLYLIGANDS JOINED TO A STABLE PROTEIN CORE

CROSS-REFERENCE TO RELATED APPLICATIONS

This is a continuation of application Ser. No. 07/646,875 filed on Jan. 28, 1991, now abandoned which is a continuation in part of application Ser. No. 07/575,394, filed Aug. 29, 1990, now abandoned.

TECHNICAL FIELD

The field of this invention is proteinaceous physiologically active polyligands.

BACKGROUND

Many of the activities of mammalian cells are controlled by the binding of ligands to surface membrane protein receptors. Thus, DNA replication and cell proliferation, differentiation, maturation, homing, metabolism, neuronal signals, and many functional capabilities can be the result of the binding of one or more ligands to the surface membrane receptors present on a cell and the transduction of a signal as a result of this binding. In some situations, such as cancer, where the cancer cells may proliferate because of autocrine reactions, there is an interest in inhibiting the signal transduction. In other situations, such as allograft rejection, it is the initial recognition by CD4 and CD8 T-cells of the graft as foreign material which in major part causes the graft to be rejected. Similarly, allogeneic bone marrow can produce graft vs. host disease, where allogeneic T-cells are included in the bone marrow implant or autoimmune diseases may involve T-cells, where inhibition of T-cell proliferation is desirable.

There are many examples where one wishes to modulate cellular response to an available ligand. Frequently, one wishes to inhibit the ligand-induced signal transduction or render its effect null. Efforts in this direction have employed monoclonal antibodies, there having been numerous reports in the literature in relation to modulating the immune system in animal models. For example, uses of antibodies against the interleukin-2 receptor (IL-2R) have been reported. Monoclonal antibodies targeting peptide receptors have also been used in humans, where a blocking antibody directed against the IL-2R was shown to inhibit the allograft rejection process. Soulillou et al., *Lancet*, (1987), 1: 1339–1342; Soulillou et al., *N. E. J. M.*, (1990) 322: 1175–1181. The advantage of this approach is that IL-2R is only expressed on graft recipient lymphocytes activated by donor antigens and not on resting lymphocytes, which are not genetically committed against donor antigens.

For the most part, the reagents used in the treatment of humans have been chimeric or humanized monoclonal antibodies or binding fragments (Fab or (Fab')$_2$) of monoclonal antibodies directed against membrane receptors. These reagents have several disadvantages in vivo, namely relatively low affinity as compared to the ligand itself, usually no or poor effector functions (complement- and antibody-dependent cytotoxicity), or furthermore, to the extent that these proteins are foreign, they elicit the synthesis of host antibodies against isotype or idiotype determinants. "Humanized" antibodies will probably avoid the incidence of antiisotype but not of antiidiotype antibodies, which later behave as blocking antibodies. In addition, several independent monoclonal antibodies are required to give a reasonable chance of reproducing in humans experimental results obtained in an animal model, owing to the possible absence of cross-reactivity.

There is, therefore, a substantial interest in providing alternative bioreagents, which may be used to inhibit physiological functions or act as mediators of cytotoxicity.

RELEVANT LITERATURE

Bacha et al., *J. Exp. Med.*, 167: 612–621 (1988) report a reagent prepared by the fusion of IL-2 and diphtheria toxin, while Lorberboum-Galski H. et al., *Proc. Natl. Acad. Sci. USA*, 85: 1922–1926, (1988) report the fusion of IL-2 with pseudomonas toxin. These reagents have been shown to bind with high affinity to the IL-2R binding site and to have cytotoxic effect. Traunecker et al., *Nature* 339: 68–70 (1989); Capon et al., *Nature* 337: 525–531 (1989) and Gregerson et al., *Archives of Virology* 111: 29–43 (1990) describe CD4-IgH or IgL constant region fusion proteins.

SUMMARY OF THE INVENTION

"Cytomulines" which can be made from compounds which are physiologically naturally occurring in a given species, particularly human, are provided, where the cytomulines are characterized by having a plurality of chains naturally linked together, having individual N- and/or C-termini, where each of the chains is extended by fusion to at least a portion of a naturally occurring ligand. Particularly, a truncated μ chain of an IgM molecule is fused to at least a binding portion of a ligand, where the ligand provides the N-terminal or C-terminal region. The resulting oligomeric compound mediates physiological effects. Such effects include:

(1) inhibition of signal transduction in cells carrying the surface membrane receptor for the ligand in question; and (2) mediation of complement-dependent cytotoxicity on cells as described in (1). In this case, the complement binding H chain will behave as a "humanized" toxin.

BRIEF DESCRIPTION OF THE DRAWINGS

FIG. 1 is the DNA sequence (SEQ ID NO. 1) and the encoded amino acid sequence (SEQ ID NO. 2) of the hybrid IL2Mu cDNA. The SalI, BamHI and XbaI sites discussed in the experimental section are indicated;

DESCRIPTION OF THE SPECIFIC EMBODIMENTS

Figure 2:
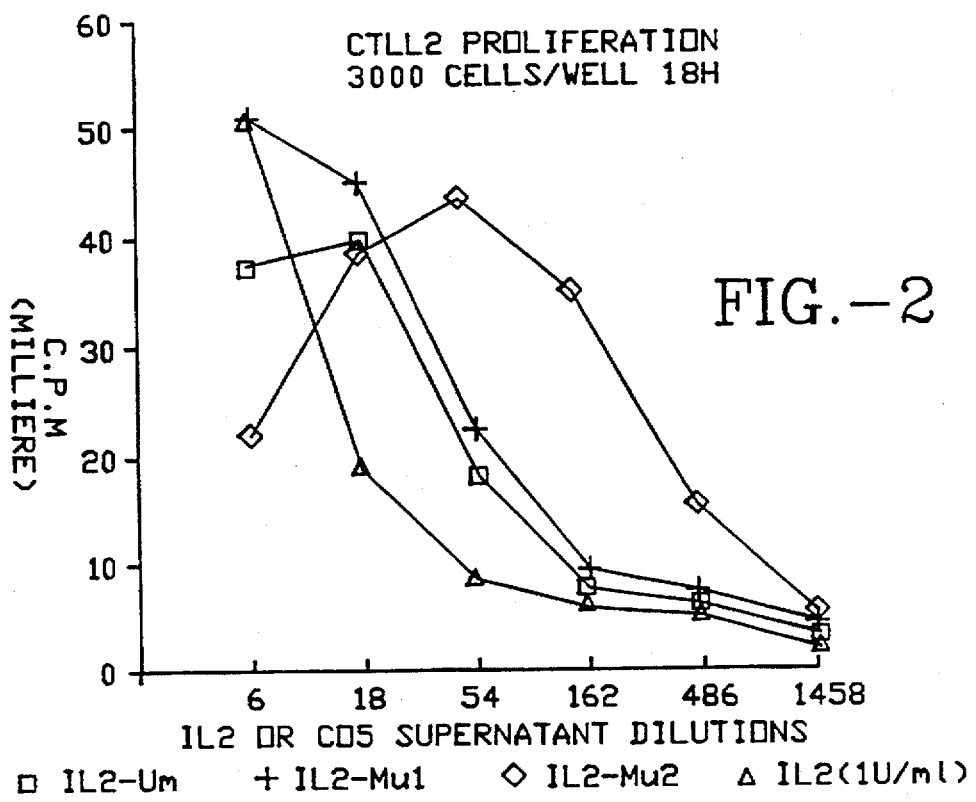
FIG. 2 is a graph of CTLL2 proliferation as indicated by a number of different fusion proteins.

Novel compositions are provided comprising fusion of chains of naturally occurring polysubunit proteins at their N- or C-termini to the complementary terminus of at least a portion of a ligand which binds to a naturally occurring surface membrane protein receptor. These fusion proteins are referred to as "cytomulines." The resulting product has a plurality of binding sites for binding to the naturally occurring receptor. Furthermore, by employing naturally occurring polysubunit proteins, the modified subunit as a result of the fusion may still be properly processed in an appropriate host organism to assemble the units and provide for the desired polysubunit assembly. Of particular interest and exemplary of polysubunit proteins is the μ chain of IgM.

The subject compositions may be characterized by the following formula:

$(L-SU)_n$ wherein:

L is the ligand or fragment thereof capable of specific binding to the naturally occurring ligand;

SU intends the subunit of a polysubunit protein, where the subunits may be joined together directly or through a central core; and n is at least 2, preferably at least 4, more preferably at least 6 and may be 10 or more, usually not more than 16, more usually not more than 10.

The polysubunit protein will have the following characteristics: (1) it will have at least two chains or subunits, preferably at least about 4 chains, more preferably at least about 6 chains; (2) it will be capable of being bound to a sequence at the N- or C-terminus, without preventing assembly of the polysubunit protein in a host organism. Where desirable, only part of the polysubunit protein may be used. Thus, for IgM μ-chains, for example, the heavy chain domain responsible for interaction with the light chain may be removed; and (3) optionally, it will have effector functions.

These characteristics are demonstrated by the μ chain of IgM or other polyunit naturally occurring proteins, or modified proteins where a cysteine is introduced into the chain of a dimeric or higher order molecule, which cysteines may than be coupled together in vitro to form a higher order oligomer. Exemplary of such proteins are MHC antigens, various members of the immunoglobulin superfamily, β-galactosidase, etc. The μ chain can form an oligomer, usually a decamer, having 10 heavy chains. However, by appropriate use of the heavy and light chains with or without the J core, the light, heavy, or both chains may be used for fusion to the ligand binding entity. Processing need not be uniform, so that mixtures of oligomers may be obtained.

Such parts of μ heavy chains as provide functions desirable in the novel fused product will be retained. Thus, if domains $CH_2$ up to $CH_4$ inclusive are retained (with part or all of domain $CH_1$ missing) in the fusion product, the latter contains adequate information for assemblage of the novel fused product able to bind complement.

Any of a wide variety of ligands of interest may be employed in the subject invention. Already, there is an extensive literature of sequences of genes encoding ligands which bind to receptors and are of interest for their physiological activity. These ligands may include such proteins as interleukins 1–7, particularly 1, 2, 3, and 4; cytokines, such as transforming growth factors -α and -β, tumor necrosis factor, epidermal growth factor, platelet derived growth factor, monocyte-colony stimulating factor, granulocyte-colony stimulating factor, granulocyte, monocyte-colony stimulating factor, erythropoietin, fibroblast growth factor, stel or stem cell growth factor, melanocyte stimulating hormone, (MSH) etc.; interferons-α, -β, and -γ; insulin, somatomedin, somatotropin, chorionic gonadotropin, and the like. In addition, major histocompatibility complex antigen binding sequences may serve as ligands.

For the most part, it may be convenient to use the entire ligand. However, in many cases, it may be desirable to use only that portion of the ligand or such extension thereof, which provides for a sufficient level of binding to produce the desired physiological effect. This will vary on a case by case basis, depending on the size of the ligand, whether that portion of the ligand which binds is known, the effect of the fusion of the sequence to the subunit on its activity, and the like. In some instances, one may fuse the two active portions of the molecule by a linking unit, which will usually be fewer than about 25 amino acids. These amino acids may provide a variety of functions, such as allowing for greater hydrophilicity or hydrophobicity at the fusion site, providing for greater access to the binding entity, or the like. Alternatively, one or more mutations, e.g. substitutions, deletions or insertions, may be introduced, usually, not more than 3 mutations. For instance, some modifications in the sequence of the μ chain can modify the complement binding capacity. It is possible that a ligand may have greater affinity when attached to the C- or N- terminus of the truncated chain. In this situation, the corresponding ligand will be attached to the appropriate terminus.

The subject compositions may be prepared by (1) Construction of a fusion gene coding for the subject composition. For this purpose, employing known genes for the two portions of the subject molecule.

(2) Expression of the fusion gene in cells. Thus, in the case of immunoglobulin fusions, genes coding for the immunoglobulin chains (heavy and/or light) may be freed of those sequences coding for the variable region and desirably the first constant region. Usually gene sequences present in the fusion gene will include those coding for the second portion of the constant region. By introducing suitable restriction enzyme sites surrounding the sequences coding for the binding entity and the polysubunit protein, or those parts of these proteins to be retained in the fused product, strategies can be elaborated to link the sequences together in the correct reading frame. The resulting fused sequence will carry an initiation codon, so that the fused gene may be expressed. The two sequences may be brought together by ligation, using PCR, recombination, or the like. Reports describing uses of such techniques abound in the literature. The particular manner in which the two portions of the fused molecule are joined is not critical to this invention and will vary depending upon the particular building blocks employed.

The various manipulations of the genes may be carried out in an appropriate cloning vector, there being a large number of such vectors readily available which provide for high efficiency of cloning, isolation, and replication. These vectors may be illustrated by pBR322, pUC series, and their derivatives. The cloning vectors will be characterized by having an appropriate replication system, a marker for selection, usually one or more antibiotic resistance genes, and one or more polylinkers, which allow for ease of introduction and excision of the sequences being cloned. After each step, the integrity of the sequence may be checked by restriction enzyme mapping, sequencing, or the like.

DNA sequences coding for dimeric proteins may be modified by in vitro mutagenesis in the region coding for C-proximal amino acids so as to code for a single cysteine not present in the originally encoded protein. Such a cysteine should be unable to form an internal disulfide bridge. For example, selecting an MHC molecule, particularly a Class II molecule the genes encoding α- and β- chains may be mutated to introduce cysteine codons. In the proteins expressed from these mutated genes, the introduced cysteines will not form a intramolecular disulfide bridge within a single chain or between the α- and β- chains of a single MHC molecule. Assembly may be achieved in vitro by activating the thiol groups by appropriate chemical modification.

The activated thiol groups will then react to intermolecular disulfide bridges to form oligomers. Other techniques for controlled linking and formation of oligomers may also be used.

In some instances it may be desired to have different ligands in the same oligomer. Where target cells have combinations of receptors, which combination is different from other cells, the higher avidity of the mixed ligand oligomer will provide for greater selectivity. Examples of such situations include resting cells as compared to stimulated cells, e.g., lymphocytes, endothelial cells etc., progenitor cells and mature or more differentiated cells, normal cells and neoplastic cells, and the like.

Once the fused gene has been prepared, it may be inserted into an appropriate expression vector to generate an expression cassette. In many cases the fused gene itself will carry the signals necessary for the initiation and termination of translation (where this is not the case, these signals will be added to the fusion gene).

Signals for initiation of transcription and RNA processing (capping, splicing, polyadenylation etc.) may be provided by the expression vector.

The expression/cassette will include a transcriptional and translational initiation region and a transcriptional and translational termination region. The transcriptional initiation region will comprise an RNA polymerase II promter, a transcriptional start site, optionally an enhancer, in some instances a sequence which provides for inducible transcription, and such other functional sequences as appropriate. For translation, usually the initiation and termination signals will be carried by the fused gene, and represent those carried by the naturally occuring genes used to make the fused gene. In some cases mutation of these sequences to increase efficiency of translation may be carried out. The transcriptional termination region will provide for a polyadenylation site and termination sequence.

The expression cassette can be transformed into an appropriate host cell in a variety of ways it may be maintained in the host. Alternatively, it may be transformed into the host under conditions whereby the expression cassette will be stably integrated into the genome of the host. In either case, it will normally have a marker for selection of the host containing it. Thus, antibiotic resistance may be employed, such as the neomycin resistance gene, which provides resistance to G418.

The expression cassette and the marker may be joined in conjunction with a replication system for extrachromosomal maintenance in the host. For the most part, mammalian replication systems will be obtained from viruses which infect mammalian cells, such as papilloma virus, adenovirus, simian virus 40, vaccinia virus, or the like. Many vectors are available comprising these replication systems, one or more markers, and a polylinker, for insertion of the expression cassette.

Transformation of the host cell may be achieved with any convenient technique, such as electroporation, calcium phosphate precipitated DNA, transfection, use of protoplasts, or the like. Methods of transforming mammalian cell hosts are well known in the literature and need not be exemplified here.

Various mammalian host cells may be employed, which are either normal or neoplastic. The cells may be lymphocytic, particularly B-lymphocytic, or non-lymphocytic, depending upon whether the processing of the μ or other chain with glycosylation is of interest. Non-secreting myeloma cell lines expressing the J chain coding gene may be also used if the μ chain is the polyunit protein core. Coexpression of J chain is not required for complement binding by a μ chain polyunit, but can increase it and facilitate the formation of large multimeric species. After transformation into the appropriate host, the cells will be grown in conventional media where the fused protein comprising the μ chain and the ligand will be expressed and assembled to form a decamer of μ chains, so as to provide for a total of 10 ligands. In this manner, one does not require the light chain. Any host cell which is employed, should not produce either heavy or light chains.

In some instances, a signal sequence may be provided which permits processing of the assembled molecule with secretion. The signal sequence may be natural to the ligand, natural to the polysubunit protein, or foreign to both. In employing a signal sequence, care should be taken that the signal sequence is removed or does not interfere with ligand binding. Signal sequence removal may be intra- or extracellular. Where secretion is obtained, assembly may provide for varied orders of oligomer. The oligomer may be modified in vitro to increase the number of subunits of the oligomer, e.g. oxidation or thiol activation, where disulfide bridging is involved.

The subject methodology may find use with any mammalian host, particularly primates, more particularly humans, and domestic animals, such as murine, bovine, caprine, ovine, canine, feline, equine, lagomorpha, etc.

The expressed product may be isolated by lysis of the host cells, isolation from the supernatant, extraction of protein, purification using electrophoresis, affinity chromatography, HPLC, or the like. The purified product may then be formulated in a variety of ways for use as a therapeutic agent. The subject product may be formulated in a variety of physiologically acceptable media, such as deionized water, saline, phosphate-buffered saline, aqueous ethanol, or the like. The concentration of the subject compounds will generally range from about 0.01 to 100 mM, depending upon the dosage level, the efficacy of the product, the nature of administration, the purpose of the administration, and the like. Generally, for similar reasons, the dosages will vary widely, ranging from about 1 pg/kg of host to about 1 mg/kg of host.

The subject compounds may also be used in the study of cells in vitro, to remove particular cells from a mixture of cells, in stimulating cells to proliferate or to inhibit stimulation and analyze the process involved with the stimulation, and the like. Where mixed ligands are involved there is a high probability that both receptors are bound simultaneously, so that the effect of prolonged simultaneous binding may be investigated.

The subject compounds may block the signals generated by a ligand binding to its receptor, by inhibiting the internalization of the complex receptor-ligand and/or kill the target cell by complement mediated cytotoxicity or other effector function, such as antibody dependent cytotoxicity (ADCC) or the like. In this way, a wide variety of events may be modulated, such as mitosis, differentiation, homing, stimulation, and the like. Thus, one may inhibit an immune response by preventing proliferation of T- and/or B-cells, prevent stimulation of T-cells by binding to MHC antigens, etc.

The following examples are offered by way of illustration and not by way of limitation.

EXPERIMENTAL

Example I

A cloned cDNA fragment containing sequences coding for the entire constant region of the human immunoglobin μ heavy chain is used as a template for polymerase chain reaction (PCR) amplification using the following primers:

SEQ ID NO. 3:

1) 5'-CGGATCCGTGATTGCTGAGCTGCCTCCC-3'

SEQ ID NO. 4:

2) 5'-CTCTAGAGGGTCAGTAGCAGGTGCCAG-3'

This leads to production of a DNA fragment containing sequences coding for the Cμ2–Cμ4 regions inclusive, lying between a BamHI cleavage site and a XbaI cleavage site. Relevant sequences (only one strand of DNA is shown) are:

SEQ ID NO. 3: (DNA) and 5 (amino acid)

5'- C GGATCC GTG ATT GCT GAG CTG CCT CCC
     BamHI    V   I   A   E   L   P   P

|----> IgM

SEQ ID NO:6 (DNA) and 7 amino acid)

--- GCT GGC ACC TGC TAC TGA CCC TCTAGAG -3'
     A   G   T   C   Y   *           XbaI

This fragment is cleaved with BamHI and XbaI and inserted between the BamHI and XbaI sites of the plasmid PKCRα. The resultant recombinant plasmid (pMu) is transformed into *E. coli* strain XL.1 and the cells grown in selective media for selection of transformed hosts which are expanded and grown in 2XTY media until the stationary state. The cells are then harvested and the product isolated and purified by standard cesium chloride density gradient techniques. Total RNA from Jurkat cells are used as a template for reverse transcription using oligo dT as primer. The resulting mixture of cDNAs is used as a template for PCR amplification using the following primers:

SEQ ID NO. 8:

1) 5'-CGTCGACTCCTGCCACAATGTACAGG-3'

SEQ ID NO. 9:

2) 5'-CGGATCCAGTCAGTGTTGAGATGATGC-3'

This leads to the production of a DNA fragment containing sequences coding for human IL-2 (including the peptide sequence) lying between cleavage sites for SalI (N-terminus) and BamHI (C-terminus). (note that the Il2 stop codon has been replaced by a BamHI cleavage sequence. Relevant sequences are (only one strand shown):

SEQ ID NO. 8:

5'- CGTCGACTCCTGCCACA ATG TAC AGG ...
    SalI               M   Y   R

SEQ ID NO:10 (DNA and 11 (amino acid)

...AGC ATC ATC TCA ACA CTG ACT GGATCC G -3'
    S   I   I   S   T   L   T   BamHI

C-Terminal Amino Acid

This fragment is cut by SalI and BamHI and introduced between the SalI and BamHI sites of pMu. The recombinant plasmid is prepared as above for pMu and called pIL2 Mu. This latter plasmid contains a SalI-XbaI fragment which codes for an IL-2—(Cμ2->Cμ4) fusion protein; the "linker" region between IL2 and μ is the sequence Gly-ser coded for by the BamHI cleavage site sequence (GGATCC)

pIL2-Mu contains the fusion gene in the expression vector pKCRα. The fusion gene is under the transcriptional control of the SV40 early gene promoter and enhancer elements while employing the splice and polyadenylation signals from a rabbit β-globin gene.

The subject plasmid is transformed into Sp2/0 cells in accordance with conventional techniques. See Junghans, et al., Cancer Research 50: 1495–1502. Since the IL2 gene carries with it the signal sequence, the product is secreted self-assembled into the supernate. In addition, assembled product is retained in the Sp2/0 cells. The cells are harvested, lysed using mild alkali, the protein product isolated free of cellular debris and purified.

Effect on IL2 dependent growth of alloreactive T-cell clones is tested for by the procedure described by Lemauff et al., Human Immunol. 19: 53–58, 1987. Effect on leukemic cell lines and leukocyte growth is shown using the same procedure. The potential capacity of the subject composition to interfere in the immune response of recipients of allografts is tested for as described by Peyronney et al., Transplant. Proc. 20; 300–302, 1988 and Soulillou et al. N. E. J. M. 322: 1175–82, 1990. Since human IL2 is cross-reactive with rat IL2 the activity of the subject composition is demonstrated in rats. Target cells are killed by mediation of complement.

Example II

Materials and Methods

Standard molecular biology techniques including the polymerase chain reaction, handling of DNA fragments, transfection of COS-1 cells using a DEAE-dextran protocol, and running of SDS-polyacrylamide gels were essentially as described in "Molecular Cloning, A Laboratory Manual, second edition", edited by Sambrook, Fritsch and Maniatis, Cold Spring Harbor Laboratory Press, Cold Spring Harbor, N.Y.

To assay supernatants containing IL2Mu or IL2Um for proliferation inducing activity, 3000 cells from the IL2 dependent CTL-L2 cell line were cultured for 18 h in the presence of either the appropriate supernatant (various dilutions were tested), medium alone, or known amounts of IL2. Cultures were pulsed with 0.5 μCi of tritiated thymidine during the last 6 h of incubation, and incorporated thymidine isolated on filters using a cell harvester. Filters were placed in vials together with 0.5 ml of scintillation fluid and the radioactivity measured using a beta counter.

Complement dependent cytotoxicity.

CTL-L2 cells were incubated with ice cold COS-1 cell supernatant for 30 min and then washed twice before the additions of rabbit complement (50% in RPMI). After 45 min of incubation of 37° C. cell viability was assayed either by counting cells under the microscope in the presence of eosin, or by measuring radioactivity released by cells which had been labeled with $Na_2^{51}CrO_4$ prior to their exposure to supernatants. Briefly, $3\times10^6$ cells were incubated with 100 μCi of $Na_2^{51}CrO_4$ for 2 h at 37° C. and then washed three times. Spontaneous release of radioactivity (SR) was that released when cells (3000/well) were incubated with medium alone, complement alone, or COS-1 cell supernatant alone. Maximum release (MR) was that obtained in the presence of 1% Triton X100. The radioactivity released when a given supernatant was used together with complement=ER. The specific cytotoxic activity=100×(ER−SR) divided by (MR−SR).

Fusion protein analysis.

COS-1 cells transfected with appropriate DNAs were cultured for 30 h in RPMI 1640 medium devoid of methionine and cysteine (Selectamine, Gibco) but containing 5% dialysed fetal calf serum and 100 μCi/ml $^{35}S$-labeled methionine and cysteine (Amersham). Supernatants were applied to a column of Affi-Gel 10 (Bio-Rad) coupled with 3 mg of a polyclonal goat anti-human IgM (mu chain specific) antibody (Biosys). The immunoaffinity matrix was then washed extensively with PBS containing 1M NaCl and 0.05% Tween 20, then with PBS diluted 10-fold in distilled water. Elution of bound material was carried out using a glycine-HCl buffer (0.2M, pH 2.5) and eluates monitored by radioactivity and optical density (280 nm) measurements. Fractions containing eluted material were immediately neutralized with Na₂HPO₄ (0.5M), pooled and dialysed against phosphate buffer (20 mM pH 7.0) before concentration using a Speed Vac. SDS-PAGE was carried out according to Laemmli on 4.5–16% polyacrylamide gradient slab gels. Before loading, lyophilized samples were heated for 3 min at 95° C. in sample buffer containing 5% 2-mercaptoethanol. After electrophoresis, gels were equilibrated with Amplify (Amersham), dried and processed for autoradiography at −70° C. Radiolabeled molecular weight standards were from Pharmacia.

RESULTS AND DISCUSSION

Hybrid cDNA construction.

The general strategy for production of immunoglobulin fusion proteins involves the replacement of the immunoglobulin variable region by the protein of interest. The immunoglobulin mu heavy chain constant region was used. The CH2–CH4 domains contain the sequences necessary to bind complement and mediate ADCC, and also the cysteine resides involved in multimerisation of the Immunoglobulin, normally found as pentamers or hexamers. The IL-2—(CH2–CH4 domain) fusion protein would form multimers which retained their ability to bind the IL2 receptor with high affinity, fix complement, and mediate ADCC.

As a first step for production of the fusion protein, a hybrid IL2 immunoglobulin mu cDNA was prepared. The cDNA population obtained from reverse transcription of total RNA isolated from transiently stimulated Jurkat cells was used as a template for PCR amplification. One primer used corresponded to a region of the 5' untranslated region of the IL2 mRNA, and was linked to a SalI cleavage sequence. The second primer was complementary to the sequences coding for the carboxy terminal amino acids of IL2, and was linked to a cleavage sequence for BamHI. In this way a SalI-BamHI fragment coding for IL2 was obtained, with the stop codon being replaced by the BamHI site. In another set of experiments a partial cDNA coding for a human immunoglobulin mu heavy chain was used as a template for PCR amplification. One primer used corresponded to sequences coding for the first amino acids of the CH2 domain, and was linked to a BamHI cleavage sequence. The other primer was complementary to sequences coding for the carboxy terminal tail of the immunoglobulin, and was linked to an XbaI cleavage sequence. In this way a BamHI-XbaI fragment coding for the CH2–CH4 domains was obtained. The two PCR products were combined via their BamHI sequences to produce the hybrid cDNA sought after. The sequence is provided in FIG. 1 (SEQ ID NO: 1). This cDNA should carry all the information necessary to specify the production of a secreted 483 amino acid fusion protein (IL2-Mu) (SEQ ID NO: 2) which can form multimers, bind to the IL2 receptor and activate complement. A variant form of the cDNA was also produced by reversing the orientation of a BstEI fragment (see FIG. 1) contained within the immunoglobulin coding sequences. This cDNA codes for a truncated 221 amino acid fusion protein (IL2Um) which lacks part of the CH2 domain and all of the CH3 and CH4 domains, and thus should be unable to form multimers or bind complement, while retaining the ability to bind to the IL2 receptor.

Expression of fusion protein.

The hybrid cDNAs were introduced into the eucaryotic expression vector pKCRα under control of the SV40 early gene promoter. COS-1 cells were transfected with the resulting plasmids or pKCRα and secreted proteins harvested for analysis. These proteins were subjected to affinity chromatography using an anti-IgM resin. Bound proteins were eluted and analyzed by SDS-PAGE under reducing conditions. This analysis of affinity purified proteins from experiments using the IL2Mu and IL2Um cDNAs permitted detection of 64 kDa and 39 kDa proteins respectively. Neither protein was detected when the pKCRα vector was used for transfection.

Both IL2Mu and IL2Um stimulate cell growth.

Having demonstrated that the hybrid cDNAs can be used to produce either IL2Mu or IL2Um, we wished to determine whether these proteins could bind to the IL2 receptor. To this end, the fusion proteins were tested for their ability to promote the growth of the IL2 dependent murine T-cell line CTL-L2 and lectin-activated human T lymphocytes. Supernatants from COS-1 cells transfected with IL2Mu or IL2Um expression vectors, unlike those from cells transfected with the "empty" expression vector pKCRα, specifically elicited the proliferation of both murine and human activated T-cells.

IL2Mu but not IL2Um binding leads to complement induced cytotoxicity.

Figure 3:
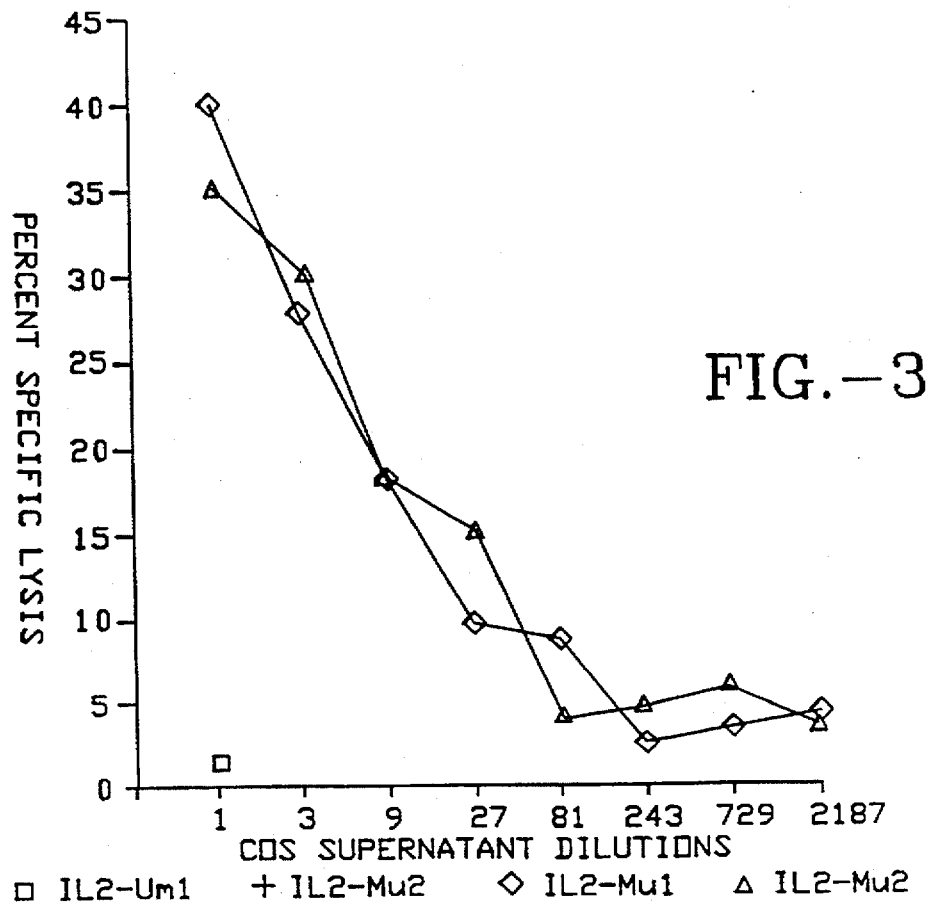
FIG. 3 is a graph of C' dependent cytotoxicity for a number of different fusion proteins.

(FIGS. 2 and 3; two different preparations of each of the fusion proteins are tested.)

In the next study it was determined whether the bound fusion proteins could be used to effect complement induced killing specific to those lymphocytes expressing a high affinity IL2 receptor. To this end, $^{51}$Cr labelled CTL-L2 lymphocytes were incubated with the reagents to be tested (supernatants from COS-1 cells transfected with the IL2Mu and IL2Um expression vectors or the pKCRα vector). Rabbit complement was added 45 min. later and the cells incubated for a further hour at 37° C. The amount of $^{51}$Cr released was then estimated and the percentage of specific cell lysis calculated. Significant lysis of CTL-L2 cells was observed after incubation with IL2Mu containing supernatants and rabbit complement, while no killing over and above that induced by the complement alone was seen when IL2Um containing supernatants and rabbit complement were used. The phenomenon was dose dependent and specific, as IL2-receptor negative cell lines (such as DA-1a mouse cells) were not killed under the same assay conditions.

Following the above procedures, the sequence encoding the IL2 ligand may be replaced with a sequence encoding any other ligand. In some situations it may be desirable to allow for a mixed composition, where some of the chains comprise a ligand for one receptor, while other chains comprise a ligand for a different receptor. Such mixed compositions may find application where the selected receptors are specific for a particular class of cells, so that the targeted population may be restricted to cells of a particular class.

In addition, the fusion proteins should have the unique advantage of not triggering any immune response from the human recipient, both its components are of human natural origin. Thus, the subject compositions may be repeatedly administered, without being inactivated by the immune system, nor inducing an immune response.

It is evident from the above description that the compounds of the subject invention provide for a unique methodology for inhibiting a wide variety of physiological processes. Thus, the multi-ligand compound can bind to a plurality of surface membrane protein receptors, and may in this manner prevent ligand internalization, hinder signal induction or kill the target cell by complement mediation. In this manner, many processes may be modulated for prophylactic or therapeutic treatment of mammalian hosts.

By employing the subject compositions, by themselves or in conjunction with other drugs, various conditions, such as graft rejection, autoimmune diseases, graft vs. host disease, and tumors, may be treated.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A DNA sequence encoding a subunit of a composition, said composition comprising at least six subunits, each subunit consisting essentially of a portion of a µ subunit constant region of IgM up to the entire µ subunit constant region of IgM capable of assembling upon expression in a cellular host, said subunits covalently joined as a result of assembling upon expression in a cellular host, each of said subunits fused to a naturally occurring peptide sequence capable of binding to a naturally-occurring receptor on a cell surface membrane.

2. A DNA sequence according to claim 1 joined to at least one of a stable replication system or a marker for selection of a cellular host.

3. An expression cassette comprising a DNA sequence according to claim 1 joined to and under the transcriptional and translational regulation of a transcriptional initiation region and a transcriptional termination region.

4. A cellular host comprising a DNA sequence according to claim 3.

5. A method of producing a composition comprising at least six subunits covalently joined, wherein said subunits comprise at least a portion of a µ chain of an immunoglobulin, which portion of said naturally occurring subunit naturally assembles upon expression in a cellular host, fused to a peptide sequence capable of binding to a naturally occurring receptor on a cell surface membrane, said method comprising:

growing a cellular host comprising a DNA sequence encoding a subunit of a composition comprising at least six subunits covalently joined, wherein said subunits comprise a portion of a naturally-occurring µ chain of an immunoglobulin, which portion of said naturally-occurring subunit naturally assembles upon expression in a cellular host, fused to a naturally-occurring peptide sequence capable of binding to a naturally-occurring receptor on a cell surface membrane, said growing occurring in an appropriate nutrient medium, whereby said composition is expressed; and isolating said composition.

6. A DNA sequence encoding a subunit of a composition comprising at least six subunits, each subunit consisting essentially of a portion of a µ subunit constant region up to th entire µ subunit constant region of IgM, covalently joined as a result of assembling upon expression in a cellular host, each of said subunits fused to a peptide sequence of human IL-2 capable of binding to the human IL-2 human receptor.

7. A DNA sequence according to claim 6, wherein said IL-2 peptide sequence is the entire IL-2 sequence and said µ subunit constant region comprises at least the CH2–CH4 portion of said constant region.

8. A DNA sequence encoding a subunit of a composition, said composition comprising at least six subunits, each subunit consisting essentially of the CH2–CH4 portion of the µ subunit constant region of IgM covalently joined as a result of assembling upon expression in a cellular host, each of said subunits fused to a naturally-occurring peptide sequence capable of binding to a naturally-occurring receptor on a surface membrane.

* * * * *